(12) United States Patent
Kistler et al.

(10) Patent No.: US 7,967,748 B2
(45) Date of Patent: Jun. 28, 2011

(54) RESILIENTLY SUPPORTED SEAL CAP FOR HAND ASSISTED LAPAROSCOPIC SURGICAL PROCEDURES

(75) Inventors: Paul H. Kistler, Cincinnati, OH (US); Andrew T. Beckman, Cincinnati, OH (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 414 days.

(21) Appl. No.: 11/611,167

(22) Filed: Dec. 15, 2006

(65) Prior Publication Data

US 2008/0146883 A1   Jun. 19, 2008

(51) Int. Cl.
*A61B 17/00* (2006.01)

(52) U.S. Cl. ........ 600/204; 606/201; 606/206; 606/207; 606/208; 606/213

(58) Field of Classification Search .................. 600/204, 600/206, 207, 208, 213
See application file for complete search history.

(56) References Cited

U.S. PATENT DOCUMENTS

| | | | |
|---|---|---|---|
| 563,645 | A | 7/1896 | Bitting |
| 564,645 | A | 7/1896 | Queen |
| 2,739,587 | A | 3/1956 | Scholl |
| 3,111,943 | A | 11/1963 | Orndorff |
| 3,332,417 | A | 7/1967 | Blanford et al. |
| 3,347,226 | A | 10/1967 | Harrower |
| 3,347,227 | A | 10/1967 | Harrower |
| 3,397,692 | A | 8/1968 | Creager, Jr. et al. |
| 5,100,420 | A | 3/1992 | Green et al. |
| 5,104,383 | A | 4/1992 | Shichman |
| 5,171,249 | A | 12/1992 | Stefanchik et al. |
| 5,197,955 | A | 3/1993 | Stephens et al. |
| 5,292,330 | A | 3/1994 | Shutt |
| 5,324,268 | A | 6/1994 | Yoon |
| 5,337,754 | A | 8/1994 | Heaven et al. |
| 5,366,478 | A | 11/1994 | Brinkerhoff et al. |
| 5,385,552 | A | 1/1995 | Haber et al. |
| 5,437,683 | A | 8/1995 | Neumann et al. |

(Continued)

FOREIGN PATENT DOCUMENTS

EP   0776180   6/1997

(Continued)

OTHER PUBLICATIONS

International Search Report dated May 28, 2008 for PCT/US2007/087372.

(Continued)

*Primary Examiner* — Thomas C Barrett
*Assistant Examiner* — Michael T Schaper
(74) *Attorney, Agent, or Firm* — Frost Brown Todd LLC (57) ABSTRACT

A laparoscopic disk assembly for a Hand Assisted Laparoscopic Surgery (HALS) procedure includes an exteriorly visible laparoscopic disk (seal cap) attached to a retractor skirt. The laparoscopic disk provides an adjustable exterior opening. A downward annular surface is supported by an attached flexible or resilient ("soft") support member that in turn forms an annular contact upon a patient's abdomen wall surrounding an incision to form a sealing connection, to facilitate improved manipulation or degrees of freedom through the laparoscopic disk without loss of insufflation pressure, to minimize, if not eliminate, bruising, to prevent rotation movement of a retractor skirt in the incision, and to reduce fatigue. Versions include a resilient pad, a resilient skirt that adheres to the patient's skin, a skirt with horizontal pleats, and a toroidal bladder that comfortably depresses into the skin.

14 Claims, 9 Drawing Sheets

U.S. PATENT DOCUMENTS

| | | | |
|---|---|---|---|
| 5,460,170 | A | 10/1995 | Hammerslag |
| 5,480,410 | A | 1/1996 | Cuschieri et al. |
| 5,514,133 | A | 5/1996 | Golub et al. |
| 5,522,791 | A | 6/1996 | Leyva |
| 5,524,644 | A | 6/1996 | Crook |
| 5,526,536 | A | 6/1996 | Cartmill |
| 5,545,179 | A | 8/1996 | Williamson, IV |
| 5,640,977 | A | 6/1997 | Leahy et al. |
| 5,649,550 | A | 7/1997 | Crook |
| 5,653,705 | A | 8/1997 | de la Torre et al. |
| 5,653,717 | A | 8/1997 | Ko et al. |
| 5,672,168 | A | 9/1997 | de la Torre et al. |
| 5,741,298 | A | 4/1998 | MacLeod |
| 5,803,921 | A | 9/1998 | Bonadio |
| 5,810,721 | A | 9/1998 | Mueller et al. |
| 5,813,409 | A | 9/1998 | Leahy et al. |
| 5,817,062 | A | 10/1998 | Flom et al. |
| 5,853,395 | A | 12/1998 | Crook et al. |
| 5,899,208 | A | 5/1999 | Bonadio |
| 5,906,577 | A | 5/1999 | Beane et al. |
| 5,925,064 | A | 7/1999 | Meyers et al. |
| 5,947,922 | A | 9/1999 | MacLeod |
| 5,957,913 | A | 9/1999 | de la Torre et al. |
| 6,024,736 | A | 2/2000 | de la Torre et al. |
| 6,033,426 | A | 3/2000 | Kaji |
| 6,033,428 | A | 3/2000 | Sardella |
| 6,048,309 | A | 4/2000 | Flom et al. |
| 6,077,288 | A | 6/2000 | Shimomura et al. |
| 6,110,154 | A | 8/2000 | Shimomura et al. |
| 6,142,935 | A | 11/2000 | Flom et al. |
| 6,142,936 | A | 11/2000 | Beane et al. |
| 6,142,946 | A | 11/2000 | Hwang et al. |
| 6,149,642 | A | 11/2000 | Gerhart et al. |
| 6,159,200 | A | 12/2000 | Verdura et al. |
| 6,165,184 | A | 12/2000 | Verdura et al. |
| 6,228,022 | B1 | 5/2001 | Friesem et al. |
| 6,254,534 | B1 | 7/2001 | Butler et al. |
| 6,315,770 | B1 | 11/2001 | de la Torre et al. |
| 6,319,246 | B1 | 11/2001 | de la Torre et al. |
| 6,382,211 | B1 | 5/2002 | Crook |
| 6,440,063 | B1 | 8/2002 | Beane et al. |
| 6,450,983 | B1 | 9/2002 | Rambo |
| 6,485,467 | B1 | 11/2002 | Crook et al. |
| 6,536,277 | B1 | 3/2003 | Chuang |
| 6,540,983 | B1 | 4/2003 | Adjei et al. |
| 6,578,577 | B2 | 6/2003 | Bonadio et al. |
| 6,582,364 | B2 | 6/2003 | Butler et al. |
| 6,589,167 | B1 | 7/2003 | Shimomura et al. |
| 6,613,952 | B2 | 9/2003 | Rambo |
| 6,623,426 | B2 | 9/2003 | Bonadio et al. |
| 6,676,706 | B1 | 1/2004 | Mears et al. |
| 6,723,044 | B2 | 4/2004 | Pulford et al. |
| 6,808,520 | B1 | 10/2004 | Fourkas et al. |
| 6,814,078 | B2 | 11/2004 | Crook |
| 6,814,700 | B1 | 11/2004 | Mueller et al. |
| 6,846,287 | B2 | 1/2005 | Bonadio et al. |
| 2001/0037053 | A1 | 11/2001 | Bonadio et al. |
| 2001/0047188 | A1 | 11/2001 | Bonadio et al. |
| 2002/0002324 | A1 | 1/2002 | McManus |
| 2002/0010389 | A1 | 1/2002 | Butler et al. |
| 2002/0038077 | A1 | 3/2002 | de la Torre et al. |
| 2002/0068923 | A1 | 6/2002 | Caldwell et al. |
| 2002/0072762 | A1 | 6/2002 | Bonadio et al. |
| 2002/0162559 | A1 | 11/2002 | Crook |
| 2002/0183594 | A1* | 12/2002 | Beane et al. ............... 600/207 |
| 2003/0062051 | A1 | 4/2003 | Rambo |
| 2003/0078478 | A1 | 4/2003 | Bonadio et al. |
| 2003/0192553 | A1 | 10/2003 | Rambo |
| 2004/0015185 | A1 | 1/2004 | Ewers et al. |
| 2004/0049099 | A1 | 3/2004 | Ewers et al. |
| 2004/0049100 | A1 | 3/2004 | Butler et al. |
| 2004/0073090 | A1 | 4/2004 | Butler et al. |
| 2004/0092795 | A1 | 5/2004 | Bonadio et al. |
| 2004/0092796 | A1 | 5/2004 | Butler et al. |
| 2004/0093001 | A1* | 5/2004 | Hamada .................. 606/190 |
| 2004/0097793 | A1 | 5/2004 | Butler et al. |
| 2004/0127772 | A1 | 7/2004 | Ewers et al. |
| 2004/0154624 | A1 | 8/2004 | Bonadio et al. |
| 2004/0249248 | A1 | 12/2004 | Bonadio et al. |
| 2004/0254426 | A1 | 12/2004 | Wenchell |
| 2004/0260153 | A1 | 12/2004 | Pulford et al. |
| 2004/0267096 | A1* | 12/2004 | Caldwell et al. ............ 600/213 |
| 2005/0020884 | A1* | 1/2005 | Hart et al. .................. 600/206 |
| 2005/0137460 | A1* | 6/2005 | Bertolero et al. ........... 600/213 |
| 2005/0148823 | A1* | 7/2005 | Vaugh et al. ................ 600/206 |
| 2005/0192483 | A1* | 9/2005 | Bonadio et al. ............. 600/208 |
| 2005/0222582 | A1 | 10/2005 | Wenchell |
| 2005/0241647 | A1 | 11/2005 | Nguyen et al. |
| 2005/0283050 | A1 | 12/2005 | Gundlapalli et al. |
| 2006/0084842 | A1 | 4/2006 | Hart et al. |
| 2006/0135977 | A1 | 6/2006 | Thompson et al. |
| 2006/0247500 | A1 | 11/2006 | Voegele et al. |
| 2008/0009834 | A1 | 1/2008 | Mialhe |
| 2008/0092034 | A1 | 4/2008 | Lim et al. |

FOREIGN PATENT DOCUMENTS

| | | |
|---|---|---|
| EP | 0845960 | 6/1998 |
| EP | 0887047 | 12/1998 |
| EP | 0887048 | 12/1998 |
| EP | 0888755 | 1/1999 |
| EP | 1000583 | 5/2000 |
| EP | 1135070 | 9/2001 |
| EP | 1312318 | 5/2003 |
| EP | 1 415 610 | 5/2004 |
| EP | 1442710 | 8/2004 |
| WO | WO 93/11811 | 6/1993 |
| WO | WO 95/22289 | 8/1995 |
| WO | WO 95/24864 | 9/1995 |
| WO | WO 95/27468 | 10/1995 |
| WO | WO 96/10963 | 4/1996 |
| WO | WO 97/07742 | 3/1997 |
| WO | WO 98/48724 | 11/1998 |
| WO | WO 99/03416 | 1/1999 |
| WO | WO 99/25268 | 5/1999 |
| WO | WO 00/24326 | 5/2000 |
| WO | WO 00/54677 | 9/2000 |
| WO | WO 01/08581 | 2/2001 |
| WO | WO 01/26558 | 4/2001 |
| WO | WO 01/45568 | 6/2001 |
| WO | WO 02/34108 | 5/2002 |
| WO | WO 03/028523 | 4/2003 |
| WO | WO 03/061480 | 7/2003 |
| WO | WO 03/077726 | 9/2003 |
| WO | WO 2004/026153 | 4/2004 |
| WO | WO 2004/030547 | 4/2004 |
| WO | WO 2004/054456 | 7/2004 |
| WO | WO 2004/075730 | 9/2004 |
| WO | WO 2004/075741 | 9/2004 |
| WO | WO 2004/096012 | 11/2004 |
| WO | WO 2004/103161 | 12/2004 |
| WO | WO 2005/009257 | 2/2005 |
| WO | WO 2006/061356 | 6/2006 |

OTHER PUBLICATIONS

U.S. Appl. No. 11/548,325, filed Oct. 11, 2006, Lim et al.
Abstract for EP 0845960.
Abstract for EP 0776180.
Abstract for EP 1135070.
International Search Report dated May 28, 2008 for Application No. PCT/US2007/087372.
International Search Report dated May 19, 2008 for Application No. PCT/US2007/087385.

* cited by examiner

RESILIENTLY SUPPORTED SEAL CAP FOR HAND ASSISTED LAPAROSCOPIC SURGICAL PROCEDURES

CROSS REFERENCE TO RELATED APPLICATION

The present application is related to two commonly-owned U.S. Patent Applications filed on even date herewith, the disclosures of which are hereby incorporated by reference in their entirety: (1) U.S. patent application Ser. No. 11/611,215, entitled "Handoscopy Interwoven Layered Seal Laparoscopic Disk"; and (2) U.S. patent application Ser. No. 11/611,193, entitled "Fully Automated Iris Seal for Hand Assisted Laparoscopic Surgical Procedures".

FIELD OF THE INVENTION

The invention generally relates to surgical access systems that facilitate sealed access across a body wall and into a body cavity during a laparoscopic surgical procedure.

BACKGROUND OF THE INVENTION

Abdominal surgery typically involves an incision in the abdominal wall large enough to accommodate a surgeon's hands, multiple instruments, and illumination of the body cavity. While large incisions simplify access to the body cavity during a surgery, it also increases trauma, requires extended recovery time, and can result in unsightly scars. In response to these drawbacks, minimally invasive surgical methods have been developed.

In minimally invasive abdominal surgery, or laparoscopic surgery, several smaller incisions are made into the abdominal wall. One of the openings is used to inflate the abdominal cavity with gas, which lifts the abdominal wall away from underlying organs and provides space to perform the desired surgery. This process is referred to as insufflation of the body cavity. Additional openings may be used to accommodate cannulas or trocars for illuminating and viewing the cavity, as well as instruments involved in actually performing the surgery, e.g., instruments to manipulate, cut, or resect organs and tissue.

Hand Assisted Laparoscopic Surgical (HALS) procedures are gaining increased acceptance as combining advantages of open surgery (e.g., tactile feedback) yet having some of the advantages of reduced scarring, reduced recovery time, and reduced incidence of complications of closed procedures. Laparoscopic disks are often used to provide an adjustable opening that allows insertion of the surgeon's hand to the insufflated body cavity, yet provides significant pneumatic sealing with or without the presence of the surgeon's hand.

While generally-known laparoscopic disks successfully support FIALS procedures, improvements to increase patient and surgeon comfort and to enhance performance are desired.

BRIEF DESCRIPTION OF THE FIGURES

The accompanying drawings, which are incorporated in and constitute a part of this specification, illustrate embodiments of the invention, and, together with the general description of the invention given above, and the detailed description of the embodiments given below, serve to explain the principles of the present invention.

DETAILED DESCRIPTION OF THE INVENTION

Referring now to FIGS. 1-4, the environment for performing an endoscopic surgical procedure within an abdomen is illustrated, herein referred to as Hand Assisted Laparoscopic Surgery (HALS). A surgeon places a hand through a HALS laparoscopic disk assembly 10 that includes an exteriorly visible laparoscopic disk (seal cap) 12 attached to a retractor skirt 14. The laparoscopic disk 12 provides an adjustable exterior opening 16 large enough to admit a surgeon's hand, yet provides sufficient pneumatic seal with or without the presence of the surgeon's hand to maintain an insufflated body cavity for the HALS procedure. An upper opening 17 of the retractor skirt 14 is attached to a lower circumference of the laparoscopic disk 12 with either or both presenting a downward annular surface 18 that is supported by an attached flexible or resilient ("soft") support member 20 consistent with aspects of the present invention. The soft support member 20 forms an annular contact upon an exterior surface 22 of the patient's abdomen wall 24 surrounding an incision 26.

The soft support member 20 may serve one or more, as well as others, of the following functions: (a) forms a sealing connection with the exterior surface 22 of the abdominal wall 24; (b) facilitates improved manipulation or degrees of freedom of the surgeon's hand or laparoscopic instrument (not shown) through the laparoscopic disk 12 without loss of insufflation pressure during a HALS procedure; (c) minimizes, if not eliminates altogether, bruising to the patient that would otherwise be the result of the laparoscopic disk 12; (d) prevents rotation movement of the retractor skirt 14 in the incision 26; and (e) reduces fatigue for the surgeon by more comfortably guiding the surgeon's hand.

The incision 26 is retracted (i.e., made wider) by a resilient waist 28 of the retractor skirt 14. A lower opening 30 of the retractor skirt 14 is defined by a flexible ring 32 that forms a lip of the retractor skirt 14 and is wider than the resilient waist 28 thereof to contact an inner surface 34 (FIG. 4) of the abdominal wall 24 around the incision 26. The flexible ring 32 allows insertion in a deformed state through the incision 26 with subsequent rebounding to the depicted relaxed, circular shape.

Figure 1:
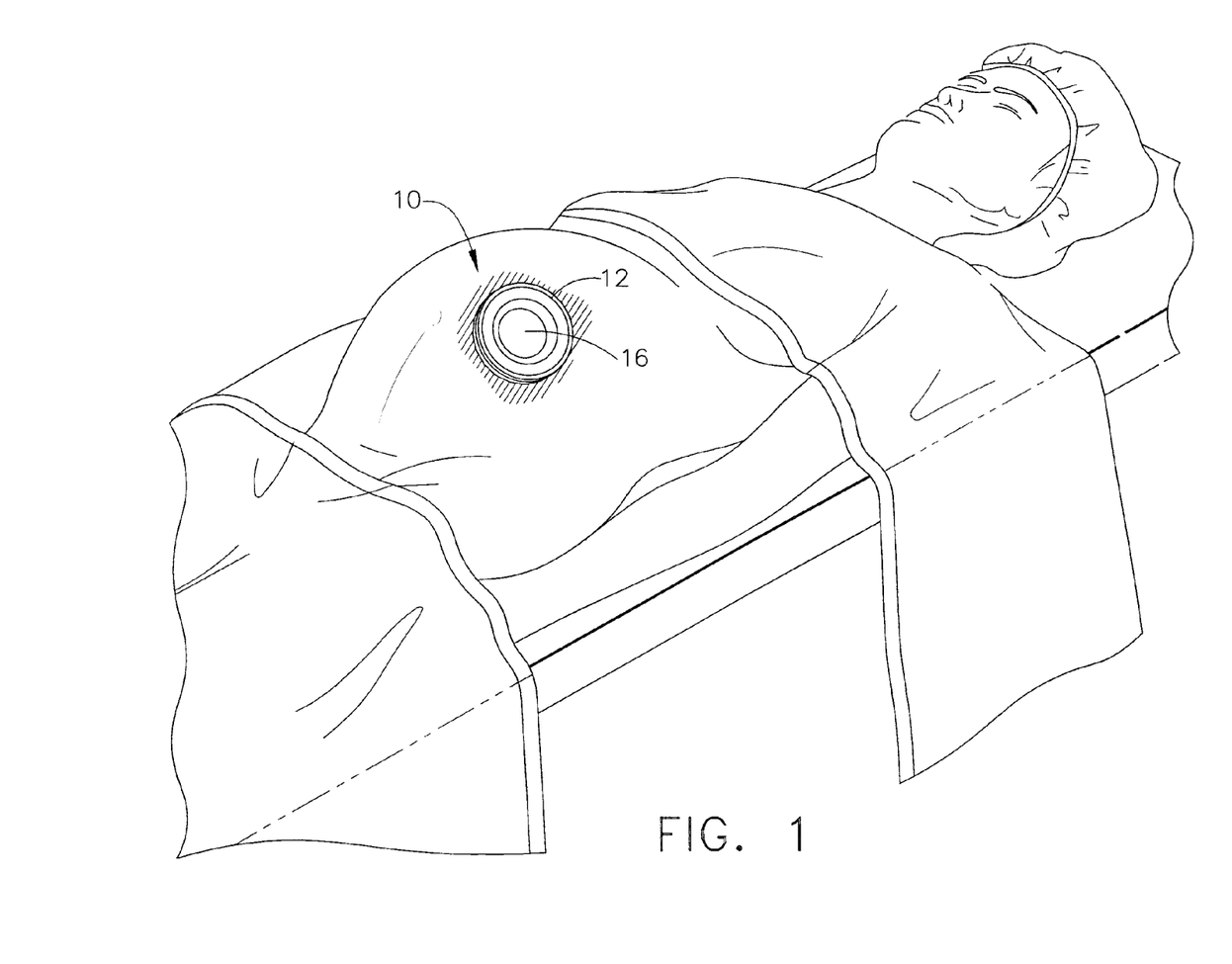
FIG. 1 is an environmental perspective view of a patient prepared for a Hand Assisted Laparoscopic Surgery (HALS) procedure by the insertion of a laparoscopic disk.
Figure 2:
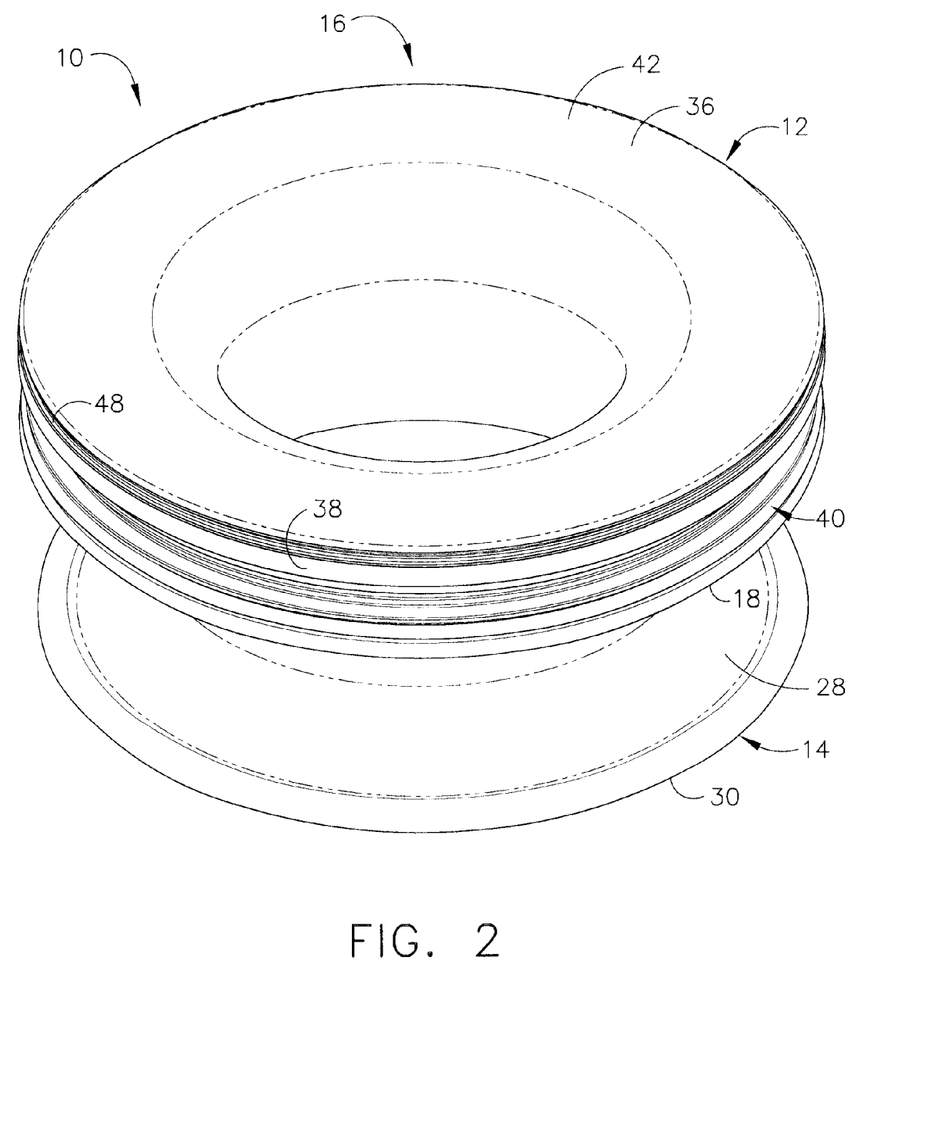
FIG. 2 is a perspective view of a FIALS laparoscopic disk assembly that includes the laparoscopic disk of FIG. 1 and incorporates a flexible or resilient ("soft") support member downwardly and annularly positioned to contact and seal to a patient's abdominal wall around an incision formed for the laparoscopic disk and attached retractor skirt.
Figure 3:
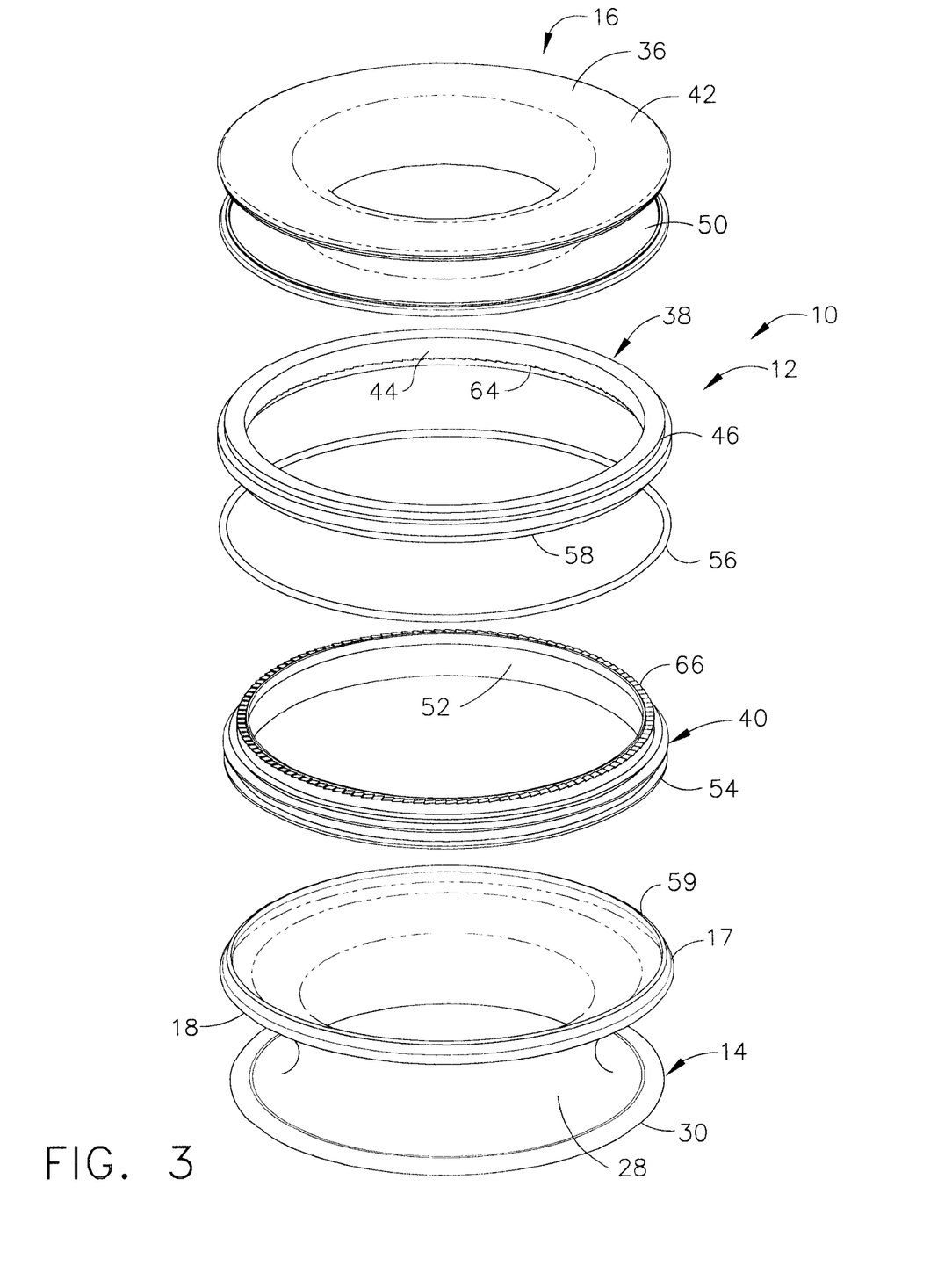
FIG. 3 is an exploded perspective view of the HALS laparoscopic disk assembly of FIG. 2.
Figure 4:
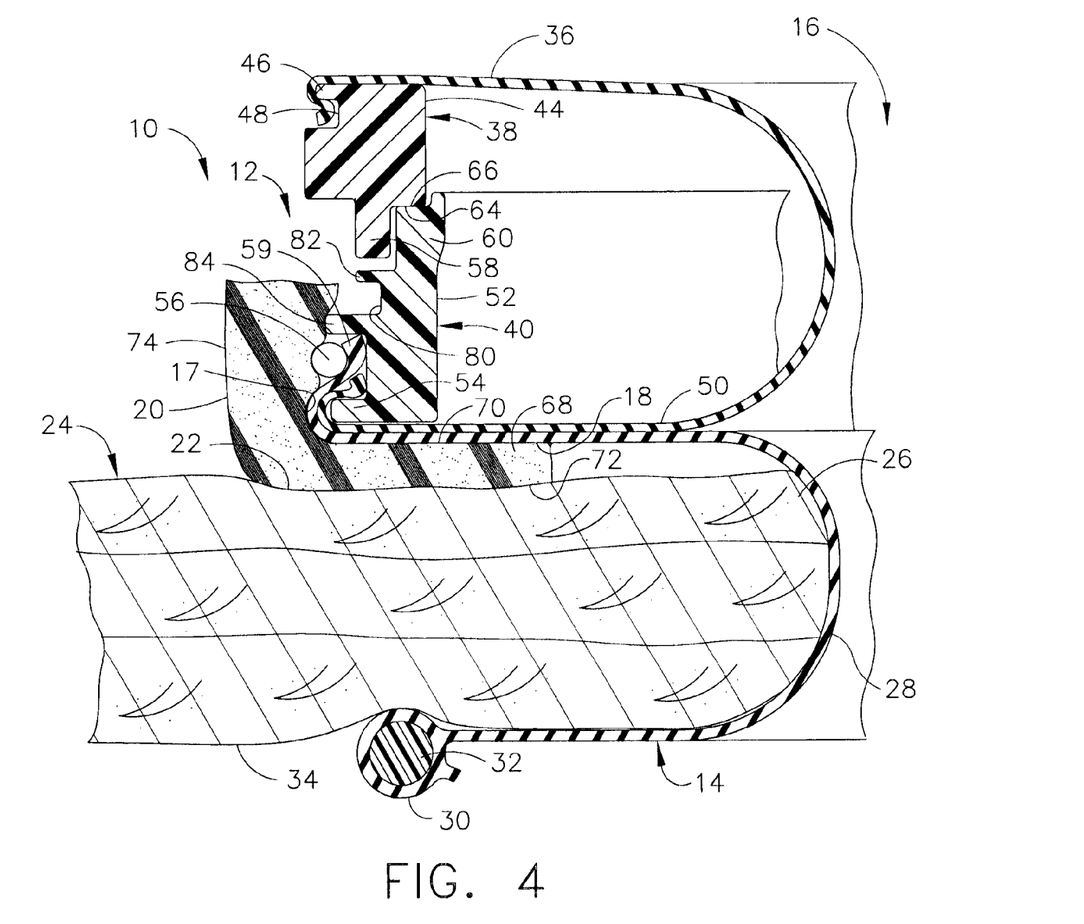
FIG. 4 is a side view taken in cross section through a left side of the HALS laparoscopic disk assembly of FIG. 2 retracting an incision through an abdominal wall and supported by the soft support member of FIG. 2 comprising a cylindrical corner pad.

In FIGS. 2-4, the adjustable opening 16 of the illustrative version of the laparoscopic disk 12 is formed by a resilient, cylindrical diaphragm 36 depicted in an open, wheel rim shape formed when stretched for attachment to a rigid upper twist ring 38 and to a rigid lower locking ring 40. In particular, an upper portion 42 of the cylindrical diaphragm 36 extends upwardly through an aperture 44 of the twist ring 38 and outwardly over an upper cylindrical rim 46 of the twist ring 38 and held by an interference fit within a ring groove 48. A lower portion 50 of the cylindrical diaphragm 36 extends downward through an aperture 52 of the locking ring 40 and is stretched outwardly to be received over a lower cylindrical rim 54 of the locking ring 40, held by a lower O-ring 56. An upper edge 59 of the retractor skirt 14 is interposed between the lower O-ring 56 and the lower portion 50 of the cylindrical diaphragm 36.

An outer, downward cylindrical lip 58 of the twist ring 40 slides downwardly around an inner, upward cylindrical lip 60 of the locking ring 40. A downward annular surface inward to the outer, downward cylindrical lip 58 of the twist ring 38 presents a downward saw tooth engaging surface 64 that engages a corresponding upward saw tooth engaging surface 66 on the inner, upward cylindrical lip 60 of the locking ring 40, resisting relative rotation between the rings 38, 40. The cylindrical diaphragm 36 is sized to draw engaging surfaces 64, 66 of the ring 38, 40 into engagement until manually separated and twisted to close the adjustable opening or thereafter twists in a return direction to open again. Alternate adjustable openings 16 are described in the two cross referenced U.S. patent application Ser. No. 11/611,193, entitled "Fully Automated Iris Seal for Hand Assisted Laparoscopic Surgical Procedures" and Ser. No. 11/611,215, entitled "Handoscopy Interwoven Layered Seal Laparoscopic Disk". The illustrative version includes the downward annular surface 18 that is provided by the retractor skirt 14 whereas these two cross referenced laparoscopic disks provide a lower surface that serves as the downward annular surface 18.

In FIG. 4, the soft support member 20 comprises a thick annular ring 68 having a top surface 70 contacting the upper edge 59 of the retractor skirt 14 and a downward surface 72 resting upon the exterior surface 22 of the patient's abdominal wall 24. The soft support member 20 also includes an upward cylindrical portion 74 that is attached and integral to the thick annular ring 68 and that conforms to an outer portion of the locking ring 40 and lower O-ring 56 to hold the soft support member 20 onto the locking ring 40, forming a cylindrical corner pad.

Figure 5:
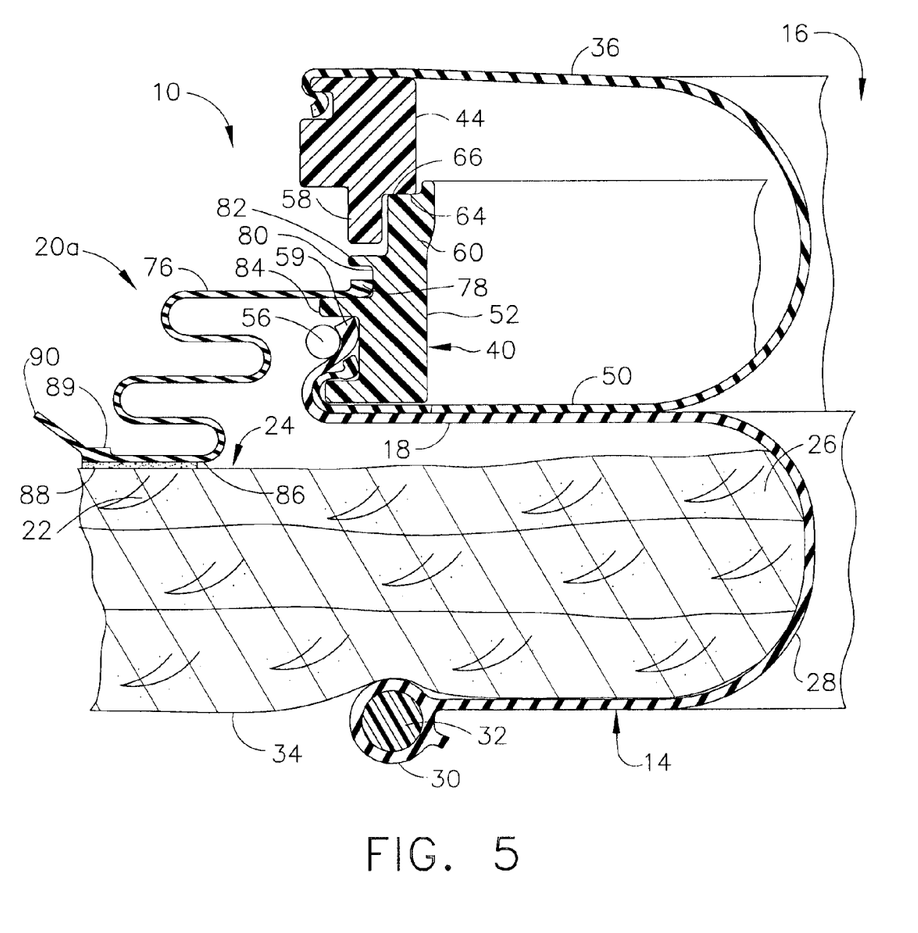
FIG. 5 is a side view taken in cross section through a left side of the HALS laparoscopic disk assembly of FIG. 2 retracting an incision through an abdominal wall and supported by an alternative soft support member comprising a horizontally pleated resilient skirt with an annular adhesive surface.

In FIG. 5, an alternative soft support member 20a comprises a horizontally pleated resilient skirt 76 that slopes generally downwardly and outwardly from an upper aperture 78 sized for engagement within an outward cylindrical groove 80 that serves as the downward annular surface of the locking ring 40 and is formed between a top outward cylindrical ridge 82 and an intermediate outward cylindrical ridge 84 that resides above, and constrains upward migration of, the lower O-ring 56. The soft support member 20a has a lower contact surface 86 onto which an annular adhesive surface 88 is attached for adhering to the exterior surface 22 of the patient's abdominal wall 24 around the incision 26. A cylindrical gasket portion 89 of rectangular cross section is formed integral to the lower contact surface 86 for stiffening to present a flat contact surface 86 when adhering to the abdominal wall 24. Thus, the horizontally pleated resilient skirt 76 that encompasses the locking ring 40 creates a pneumatic seal that captures a volume of air that cushions the laparoscopic disk 12 from the abdominal wall 24. A bottom annular lip 90 of the resilient skirt 76 extends outwardly and slightly upwardly from the lower contact surface 86 to present a gripping surface for removal of the annular adhesive surface 88 from the abdominal wall 24.

Figure 6:
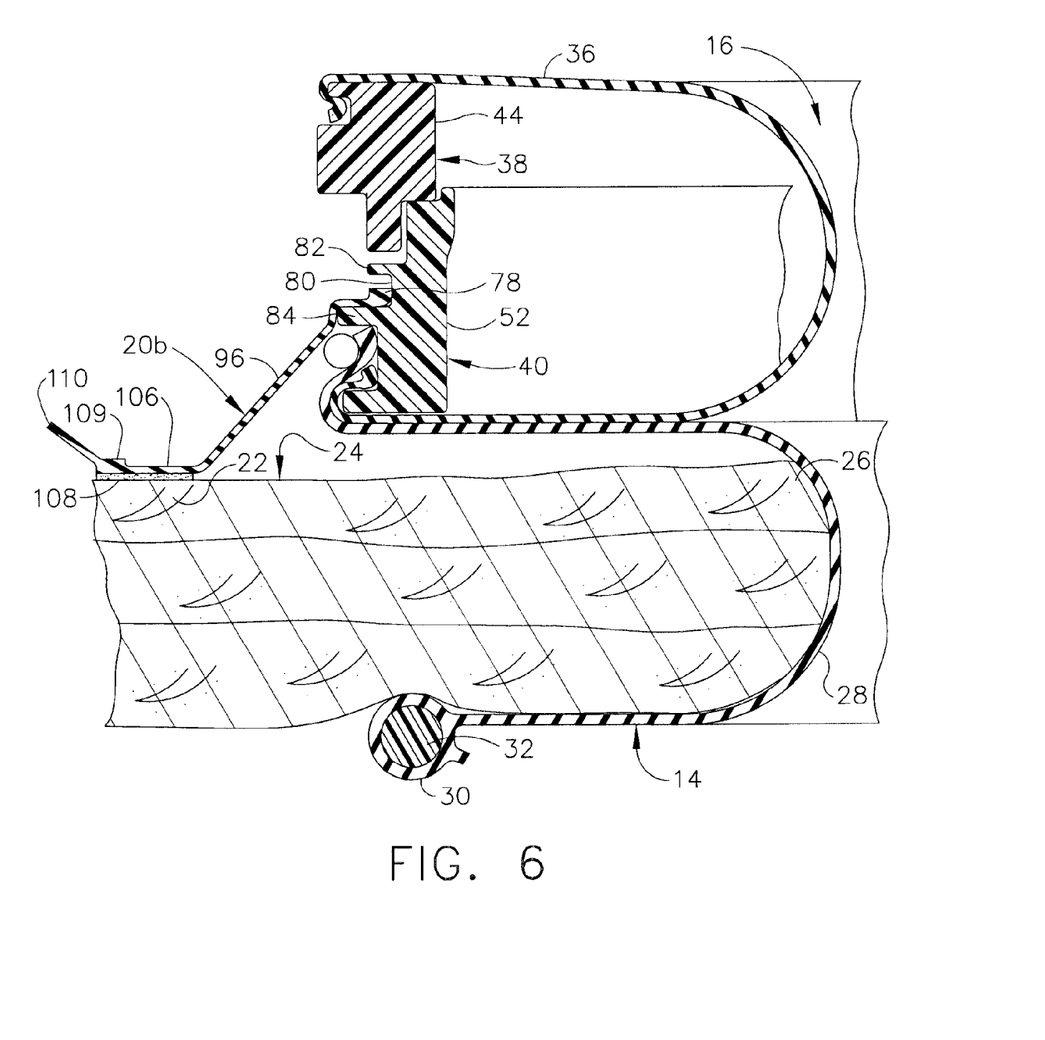
FIG. 6 is a side view taken in cross section through a left side of the HALS laparoscopic disk assembly of FIG. 2 retracting an incision through an abdominal wall and supported by another alternative soft support member comprising an outwardly and downwardly sloped resilient skirt with an annular adhesive surface.

In FIG. 6, another alternative soft support member 20b comprises a resilient skirt 96 that slopes downwardly and outwardly from an upper aperture 78 sized for engagement within the outward cylindrical groove 80 of the locking ring 40. The soft support member 20b has a lower contact surface 106 onto which an annular adhesive surface 108 is attached for adhering to the exterior surface 22 of the patient's abdominal wall 24 around the incision 26. A cylindrical gasket portion 109 of the rectangular cross section is formed integral to the lower contact surface 106 for stiffening to present a flat contact surface 106 when adhering to the abdominal wall 24. Thus the horizontally pleated resilient skirt 96 that encompasses the locking ring 40 creates a pneumatic seal that captures a volume of air that cushions the laparoscopic disk 12 from the abdominal wall 24. A bottom annular lip 110 of the resilient skirt 96 extends outwardly and slightly upwardly from the lower contact surface 106 to present a gripping surface for removal of the annular adhesive surface 108 from the abdominal wall 24.

Figure 7:
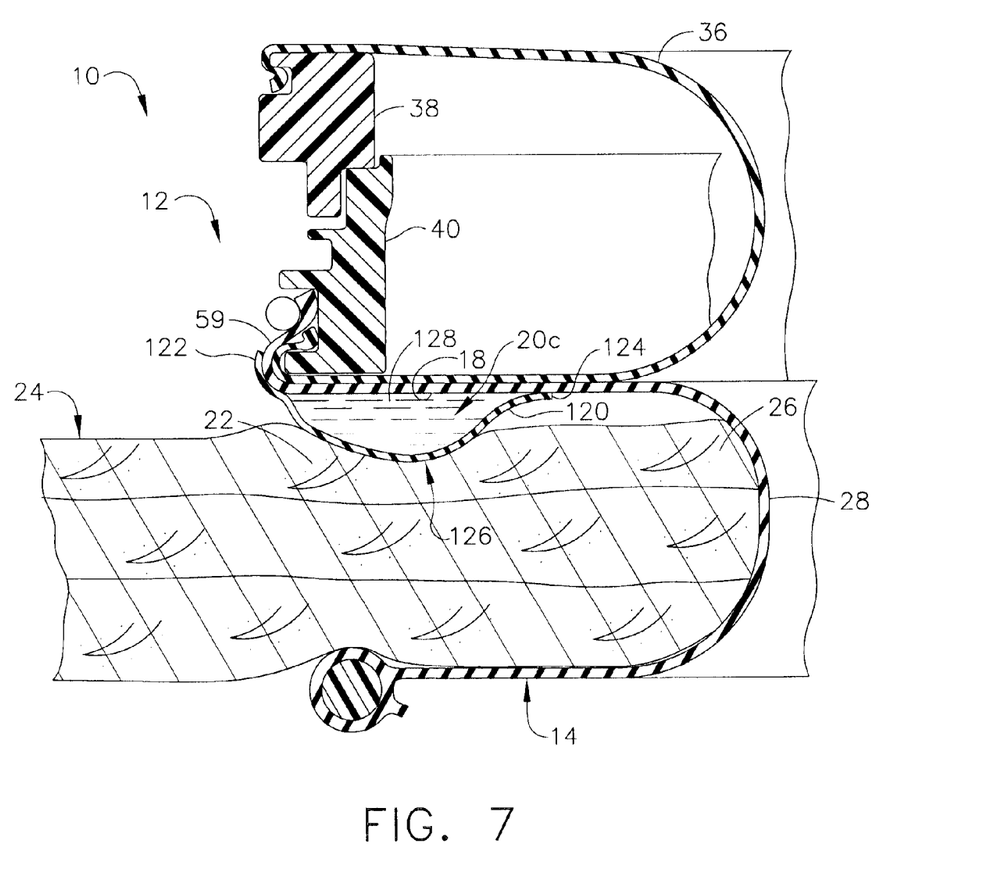
FIG. 7 is a side view taken in cross section through a left side of the HALS laparoscopic disk assembly of FIG. 2 retracting an incision through an abdominal wall and supported by an additional alternative soft support member comprising an annular resilient barrier attached to the downward annular surface formed by the retractor skirt and filled to form an annular bladder that comfortably depresses onto the abdominal wall.

In FIG. 7, an additional alternative soft support member 20c comprises a resilient annular barrier 120 attached along an outer circumference 122 to the curled, upper edge 59 of the retractor skirt 14 and along an inner circumference 124 also attached to the retractor skirt 14 that forms the downward annular surface 18 and creates an annular, downwardly extending bladder 126 that contains a gaseous, liquid, gel or resilient material 128 that comfortably presses against the exterior surface 22 of the abdominal wall 24 to form a seal and to provide support to the laparoscopic disk 12.

Figure 8:
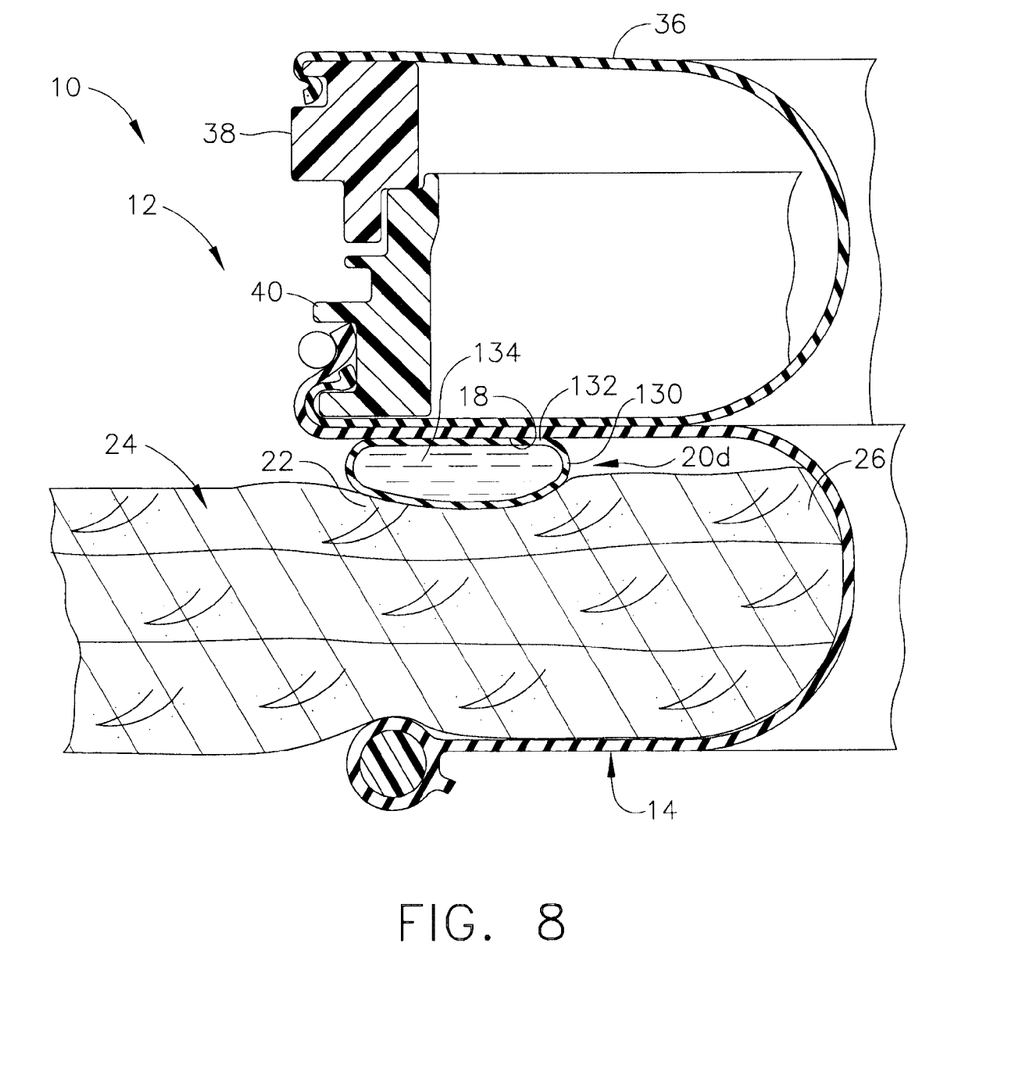
FIG. 8 is a side view taken in cross section through a left side of the HALS laparoscopic disk assembly of FIG. 2 retracting an incision through an abdominal wall and supported by a further alternative soft support member comprising a toroidal (inner tube) bladder attached to the downward annular surface formed by the retractor skirt that comfortably depresses onto the abdominal wall.

In FIG. 8, a further alternative soft support member 20d comprises a resilient toroidal bladder ("inner tube") 130 attached along an upper surface 132 to the upper portion the retractor skirt 14 that forms the downward annular surface 18. The toroidal bladder 130 contains a gaseous, liquid, gel or resilient material 134 that comfortably presses against the exterior surface 22 of the abdominal wall 24 to form a seal and to provide support to the laparoscopic disk 12.

Figure 9:
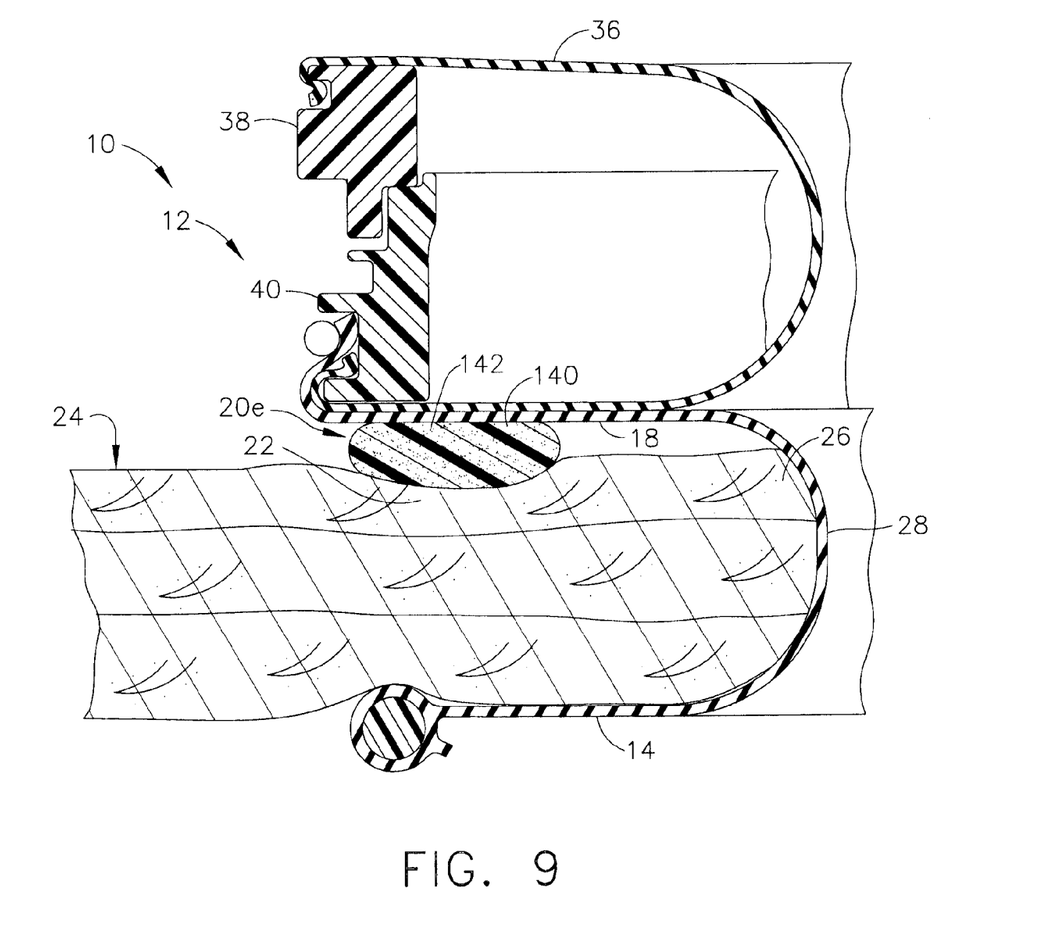
FIG. 9 is a side view taken in cross section through a left side of the HALS laparoscopic disk assembly of FIG. 2 retracting an incision through an abdominal wall and supported by a further alternative soft support member comprising a resilient toroidal pad attached to the downward annular surface formed by the retractor skirt that comfortably depresses onto the abdominal wall.

In FIG. 9, yet a further alternative soft support member 20e comprises a resilient toroidal pad 140 attached along an upper surface 142 to the upper portion of the retractor skirt 14 that forms the downward annular surface 18 that comfortably presses against the exterior surface 22 of the abdominal wall 24 to form a seal and to provide support to the laparoscopic disk 12.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

While the present invention has been illustrated by description of several embodiments and while the illustrative embodiments have been described in considerable detail, it is not the intention of the applicant to restrict or in any way limit the scope of the appended claims to such detail. Additional advantages and modifications may readily appear to those skilled in the art.

What is claimed is:

1. A device, comprising:
    a laparoscopic disk comprising an adjustable opening sized to admit and substantially pneumatically seal to a surgeon's hand, wherein the laparoscopic disk comprises a rigid upper ring, a rigid lower ring, and a cylindrical diaphragm, wherein the cylindrical diaphragm has an engagement portion presenting an upper surface and a lower surface, wherein the cylindrical diaphragm defines the adjustable opening, wherein the upper ring is rotatable relative to the lower ring to adjust the size of the adjustable opening;
    a retractor skirt comprising an upper opening attached to the lower ring of the laparoscopic disk, and a waist portion aligned with the adjustable opening for passing through and retracting an incision in an abdominal wall, wherein the retractor skirt presents a downwardly facing annular contact surface, wherein part of the cylindrical diaphragm is sandwiched between the retractor skirt and the lower ring; and
    an annular support member having an upper surface that is attached to the downwardly facing annular contact surface of the retractor skirt, wherein a patient contacting lower portion of the annular support member is located below the downwardly facing annular contact surface of the retractor skirt such that the downwardly facing annular contact surface of the retractor skirt is located above the patient contacting lower portion of the annular support member, wherein part of the retractor skirt is apposed between the upper surface of the annular support member and the lower surface of the engagement portion of the cylindrical diaphragm, and such that a portion of the retractor skirt is positioned between the upper surface of the annular support member and a lower surface of the lower ring, wherein a lower surface of the patient contacting lower portion of the annular support member is positioned to contact an exterior surface of the abdominal wall surrounding the incision.

2. The device of claim 1, wherein the annular support member comprises an annular resilient pad.

3. The device of claim 2, wherein the annular support member further comprises a cylindrical portion gripping a lower, outer portion of the laparoscopic disk and attached to the annular resilient pad.

4. The device of claim 1, further comprising an annular adhesive surface affixed to a lower surface of the annular support member.

5. The device of claim 4, wherein the lower surface further comprises a circular gasket portion.

6. The device of claim 1, wherein the annular support member comprises a bladder.

7. The device of claim 6, wherein the bladder comprises a toroidal tube.

8. The device of claim 6, wherein the bladder comprises an annular barrier attached along outer and inner circumferences to the downward annular contact surface, 9. The device of claim 6, wherein the bladder further comprises a liquid content.

10. The device of claim 6, wherein the bladder further comprises a gel content.

11. The device of claim 6, wherein the bladder further comprises a gaseous content.

12. A hand seal device, comprising:
    a laparoscopic disk assembly, the laparoscopic disk assembly comprising:
        an upper ring,
        a lower ring, wherein the lower ring has a lower horizontal surface and an outer vertical surface, wherein the lower horizontal surface of the lower ring and the outer vertical surface of the lower ring are joined at an outer lower corner of the lower ring, and
        a seal defining an opening, wherein the seal is secured to the upper ring, wherein the seal is configured to substantially pneumatically seal to a surgeon's hand;
    a retractor skirt comprising an upper portion, a lower portion, and a waist portion, wherein the upper portion is secured to the lower ring, wherein the lower portion is positionable within a patient's abdomen, wherein the waist portion extends between the upper portion and the lower portion, wherein the waist portion defines an opening aligned with the opening defined by the seal; and
    an annular support pad, wherein the annular support pad comprises a soft material, wherein the annular support pad comprises a first portion and a second portion, wherein the first portion is substantially horizontally oriented and extends radially inward below the lower horizontal surface of the lower ring, wherein the second portion is substantially vertically oriented and extends axially upward along the outer vertical surface of the lower ring, wherein the second portion of the annular support pad is positioned adjacent to the upper portion of the retractor skirt, below the lower ring, wherein the first portion of the annular support pad and the second portion of the annular support pad are joined at an inner lower corner of the annular support pad, such that the outer lower corner of the lower ring is nested in the inner lower corner of the annular support pad, with a portion of the retractor skirt and a portion of the seal being apposingly positioned between the outer lower corner of the lower ring and the inner lower corner of the annular support, wherein the annular support pad is configured to engage the exterior of the patient's abdomen.

13. The hand seal device of claim 12, wherein the second portion of the annular support pad is secured to the outer vertical surface of the lower ring.

14. A hand seal device, comprising:
a laparoscopic disk assembly, the laparoscopic disk assembly comprising:
   an upper ring, wherein the upper ring defines a central axis,
   a lower ring, wherein the lower ring has a lower surface, wherein the lower ring defines a central axis aligned with the central axis of the upper ring, and
   a seal defining an opening, wherein the seal is secured to the upper ring, wherein the seal is configured to substantially pneumatically seal to a surgeon's hand;
a retractor skirt comprising an upper portion, a lower portion, and a waist portion, wherein the upper portion is secured to the lower ring, wherein the lower portion is positionable within a patient's abdomen, wherein the waist portion extends between the upper portion and the lower portion, wherein the waist portion defines an opening aligned with the opening defined by the seal; and
an annular support member, wherein the annular support member comprises a skirt extending radially outwardly relative to the central axes defined by the upper and lower rings, wherein the skirt comprises a first portion and a cylindrical gasket portion configured to be adhered to the exterior of the patient's abdomen such that the adhered skirt of the annular support member and the retractor skirt together provide a pneumatically sealed volume of space adjacent to the patient's abdomen to provide an air cushion for the laparoscopic disk assembly, the air cushion being located between the lower surface of the lower ring and the patient's abdomen, wherein the skirt assembly terminates in a radially outwardly extending lip, wherein the radially outwardly extending lip extends radially outwardly relative to the central axes defined by the upper and lower rings, wherein the first portion of the skirt extends outwardly from the lower ring, wherein the gasket portion extends outwardly from the first portion of the skirt, wherein the radially outwardly extending lip extends outwardly from the gasket portion, wherein the radially outwardly extending lip also extends upwardly to present a gripping surface configured to be grasped by an operator when the gasket portion is adhered to the exterior of the patient's abdomen, wherein the radially outwardly extending lip is further operable to be gripped and pulled away from the exterior of the patient's abdomen to disengage the gasket portion from the exterior of the patient's abdomen to break the pneumatic seal provided in part by the adhered skirt.

* * * * *